United States Patent
Vivian

(10) Patent No.: US 12,303,643 B2
(45) Date of Patent: May 20, 2025

(54) INTUBATION APPARATUS AND METHOD OF USE

(71) Applicant: Genesis Airway Innovations Pty Ltd, Eumundi (AU)

(72) Inventor: Vernon Vivian, Cooroy (AU)

(73) Assignee: GENESIS AIRWAY INNOVATIONS PTY LTD, Eumundi (AU)

( * ) Notice: Subject to any disclaimer, the term of this patent is extended or adjusted under 35 U.S.C. 154(b) by 827 days.

(21) Appl. No.: 17/424,099

(22) PCT Filed: Jan. 22, 2020

(86) PCT No.: PCT/AU2020/050035
§ 371 (c)(1),
(2) Date: Jul. 19, 2021

(87) PCT Pub. No.: WO2020/150775
PCT Pub. Date: Jul. 30, 2020

(65) Prior Publication Data
US 2022/0096766 A1    Mar. 31, 2022

(30) Foreign Application Priority Data

Jan. 23, 2019 (AU) ................................ 2019900208
Dec. 20, 2019 (AU) ................................ 2019904876

(51) Int. Cl.
*A61M 16/04* (2006.01)
*A61M 16/08* (2006.01)

(52) U.S. Cl.
CPC .... *A61M 16/0409* (2014.02); *A61M 16/0434* (2013.01); *A61M 16/0488* (2013.01);
(Continued)

(58) Field of Classification Search
CPC .......... A61M 16/0409; A61M 16/0434; A61M 16/0488; A61M 16/0875; A61M 16/0461;
(Continued)

(56) References Cited

U.S. PATENT DOCUMENTS 4,892,095 A * 1/1990 Nakhgevany ..... A61M 16/0461
128/207.14
5,024,220 A * 6/1991 Holmgreen ....... A61M 16/0463
128/207.14
(Continued)

FOREIGN PATENT DOCUMENTS

WO    1998016273 A1    4/1998
WO    2008127994 A1   10/2008

OTHER PUBLICATIONS

PCT International Search Report and Written Opinion dated Mar, 19, 2020 for Intl. App. No. PCT/AU2020/050035, from which the instant application is based, 17 pgs.

*Primary Examiner* — Tu A Vo
*Assistant Examiner* — Kelsey E Baller
(74) *Attorney, Agent, or Firm* — Fredrikson & Byron, P.A.

(57) ABSTRACT

An intubation apparatus and, method of use, for intubating a patient. The apparatus includes an airway ventilation device having tubing located between an inlet end and an outlet end, the outlet end being configured to be locatable in the airway of a patient, intermediary tubing having a first end releasably connectable to the inlet end of the airway ventilation device and a second end having a fitting configured to connect to a gas supply, and an introducer having a first end that is alternatively releasably connectable to the first end of the intermediary tubing and a second end having a blunt tip.

5 Claims, 8 Drawing Sheets

(52) U.S. Cl.
CPC ..... *A61M 16/0875* (2013.01); *A61M 16/0461* (2013.01); *A61M 2210/0618* (2013.01); *A61M 2210/0625* (2013.01); *A61M 2210/1028* (2013.01); *A61M 2210/1046* (2013.01)

(58) Field of Classification Search
CPC .............. A61M 16/0816; A61M 16/04; A61M 16/044; A61M 2210/0618; A61M 2210/0625; A61M 2210/1028; A61M 2210/1046
See application file for complete search history.

(56) References Cited

U.S. PATENT DOCUMENTS

| | | | | |
|---|---|---|---|---|
| 5,492,538 | A * | 2/1996 | Johlin, Jr. ......... | A61M 25/0127 |
| | | | | 604/528 |
| 8,561,605 | B2 * | 10/2013 | Davis ................ | A61M 16/0431 |
| | | | | 128/207.14 |
| 2001/0032646 | A1 * | 10/2001 | Christopher ........... | A61B 1/267 |
| | | | | 128/200.26 |
| 2004/0099273 | A1 * | 5/2004 | Wright ............... | A61M 16/0084 |
| | | | | 128/207.18 |
| 2005/0268917 | A1 * | 12/2005 | Boedeker .............. | A61M 16/04 |
| | | | | 128/207.14 |
| 2008/0041391 | A1 | 2/2008 | Worley | |
| 2017/0232216 | A1 | 8/2017 | Nave et al. | |
| 2019/0134338 | A1 | 5/2019 | Mansi | |

* cited by examiner

INTUBATION APPARATUS AND METHOD OF USE

RELATED APPLICATIONS

This application is a 35 U.S.C. 371 national stage filing from International Application No. PCT/AU2020/050035, filed Jan. 22, 2020, which claims priority to Australian Application No. 2019904876, filed 2019 Dec. 20 and Australian Application No. 2019900208, filed 2019 Jan. 23, the teachings of which are incorporated herein by reference.

FIELD OF THE INVENTION

This invention relates to an intubation apparatus and method of use, preferably, but not necessarily limited to, a laryngeal mask or endotracheal tube that is capable of interchangeable oral and nasal intubation and a method of use thereof.

BACKGROUND TO THE INVENTION

Reference to background art herein is not to be construed as an admission that such art constitutes common general knowledge.

Airway intubation, such as tracheal intubation or supraglottic intubation often referred to as simply 'intubation', is the placement of tubing into a patient to maintain an open airway or for the administration of inhalational anaesthetic agents into the lungs. Such intubation is typically carried out with an endotracheal tube and/or laryngeal mask airway (LMA), often referred to as simply 'laryngeal mask'.

Such laryngeal masks have been in use for decades and have, to some extent, superseded endotracheal tubes to maintain an airway while delivering anaesthesia to a patient as they are typically easier, faster and take less skill to deploy. Laryngeal masks are also typically less invasive and better tolerated by patients with minimal haemodynamic disturbance. They can assist with smooth recovery with less discomfort such as coughing.

Laryngeal masks are inserted orally and are therefore not suitable in all cases. For example, some surgical procedures such as, but not limited to, dental and maxillofacial surgery, require a surgeon to have unfettered access to the mouth of a patient. In such situations a laryngeal mask is an obstruction and nasal endotracheal tubes are typically used to maintain an airway instead. However, nasal endotracheal intubation is difficult requiring a skilled, experienced anaesthetist with frequent complications arising such as, for example, epistaxis and damage to nasal structures. This can result in high levels of morbidity and even, in some extreme cases, fatalities.

Notwithstanding the relative simplicity of using a laryngeal mask, endotracheal tubes are generally regarded as one of the best methods of protecting and maintaining an airway in a patient. In some situations it is desirable, or even necessary, to re-intubate a patent from the oral route to the nasal route. For example, to allow for surgical access such as patients intubated for severe facial trauma or bleeding oesophageal varices. In maxillofacial surgery patients are often intubated orally in an emergency room and subsequently require nasal intubation for surgical access. Similarly, in patient transport an oral tube may be replaced with a nasal tube as it is better secured.

Changing from oral to nasal intubation in such cases typically involves removing the endotracheal tube or laryngeal mask and intubating nasally as described hereinbefore. However, such a process results in the airway of the patient being unsecured during the time period between the endotracheal tube or laryngeal mask being removed and the nasal endotracheal tube being secured. The same of course applies should a medical practitioner want to change a patient from nasal intubation to oral intubation for some reason.

Practitioners unskilled in the art of nasotracheal intubation often intubate orally first then pass a second nasal endotracheal tube until in the oropharynx before removing the oral intubated endotracheal tube and completing nasal intubation. This method, however, is time consuming and requires the patient to be intubated twice with two separate endotracheal tubes.

OBJECT OF THE INVENTION

It is an aim of this invention to provide an intubation apparatus, and/or method of use thereof, which overcomes or ameliorates one or more of the disadvantages or problems described above, or which at least provides a useful or commercial alternative.

Other preferred objects of the present invention will become apparent from the following description.

SUMMARY OF INVENTION

In one form, although it need not be the only or indeed the broadest form, there is provided an intubation apparatus including:
  an airway ventilation device having tubing located between an inlet end and an outlet end, the outlet end being configured to be locatable in the airway of a patient;
  intermediary tubing having a first end releasably connectable to the inlet end of the airway ventilation device and a second end having a fitting configured to connect to a gas supply; and
  an introducer having a first end releasably connectable to the first end of the intermediary tubing and a second end having a blunt tip.

The airway ventilation device may have at least one inflatable component. The inflatable component may be located at or adjacent the outlet end of the airway ventilation device. The inflatable component may include a cuff. The inflatable component may be inflated via an inflation line. The inflation line may include a valve. The inflation line may include a balloon, preferably a pilot balloon. The airway ventilation device may include a laryngeal mask. The airway ventilation device may include an endotracheal tube. The airway of a patient may include the trachea and/or supraglottic region of the patient.

The inlet end of the airway ventilation device may include a connector to facilitate connection of the inlet end of the airway ventilation device with the first end of the intermediary tubing. The first end of the intermediary tubing may include a connector to facilitate connection to the inlet end of the airway ventilation device.

The connector may include a hollow member. The hollow member may include at least one hollow protrusion. The hollow protrusion may be annular. At least a portion of the hollow protrusion may have an outer diameter that is less than the outer diameter of the tubing of the airway ventilation device. The connector may have an outer diameter that is the same, or substantially the same, as the inner diameter of the tubing. The connector preferably has an outer diameter that is no greater than the outer diameter of the tubing of the airway ventilation device. The connector may include a flange. The flange may have an outer diameter that is the same, or substantially the same, as the outer diameter of the tubing.

The connector may be integral with the inlet end of the tubing or the first end of the intermediary tubing. Alternatively, the connector may be a removable component in the form of an adapter configured to connect the inlet end of the tubing to the first end of the intermediary tubing. The connector may include two aligned hollow protrusions separated by a flange. The inlet end of the airway ventilation device and the first end of the intermediary tubing may have a diameter that is no greater than the outer diameter of adjacent tubing. The connector may have a diameter that is no greater than the outer diameter of adjacent tubing.

The fitting of the intermediary tubing may include a standardised fitting for gas supply connection. The fitting may include a 15 mm airway connector. The fitting may be removable. The fitting may be interchangeable. In an alternative embodiment, the fitting may be located on the inlet end of the airway ventilation device. The fitting of the airway ventilation device is preferably removable and/or interchangeable between having a standardised fitting for gas supply and being connectable to the first end of the intermediary tubing. A connector for connecting the inlet end of the airway ventilation device to the first end of the intermediary tubing may be located at the inlet end of the airway ventilation device or at the first end of the intermediary tubing. The connector may comprise two connectable parts, with a portion of each being located on each of the inlet end of the airway ventilation device or at the first end of the intermediary tubing. The intermediary tubing may be solid. The solid intermediary tubing may be in configured to pull the inlet end of the airway ventilation device through the nasopharynx of a patient to provide a retrograde nasal intubation of the airway ventilation device.

The intubation apparatus may include two intermediary tubings. A first intermediary tubing may be of a first length and a second intermediary tubing may be of a second length. The second intermediary tubing may have a greater length than the first intermediary tubing. The first intermediary tubing may be adapted for oral intubation and the second intermediary tubing may be adapted for nasal intubation. The first intermediary tubing and the second intermediary tubing may be interchangeable.

The introducer may include an elongate body between the first end and the second end. At least a portion of the elongate body may be tapered. The taper may reduce a diameter of the elongate body from the first end to the second end. The introducer may be tapered continually between the first end and second end. At least a portion of the elongate body may be flexible. At least a portion of the elongate body may be curved. The introducer may include a head having a shaft adapted to be received inside the first end of the intermediary tubing. The head may have a socket adapted to receive a connector located on the first end of the intermediary tubing. The introducer may include a boss around at least a portion of the shaft. The introducer may be integrally formed.

The shaft of the introducer may further include a projection. The projection may correspond to an opening in a respective tube that receives the shaft. The projection may be substantially circular or oval in shape. The projection may extend perpendicularly to the longitudinal axis of the introducer. The projection may extend perpendicularly to approximately the height of the boss. The boss may be shaped. The boss shape may correspond to an end of an endotracheal tube, e.g. a straight, bevelled, curved, Murphy, or Magill tipped endotracheal tube. The introducer is may be made integrally from a resiliently flexible material such as a latex free rubber. It should be appreciated that other materials, such as suitably flexible plastics, may be utilised.

According to another form, there is provided a method of intubating a patient, preferably utilising an intubation apparatus as hereinbefore described, the method including:

inserting an outlet end of an airway ventilation device in the airway of a patient;

passing an introducer having a first end connected to intermediary tubing and a second end having a blunt tip through the nasopharynx of a patient;

pulling the introducer through the mouth of the patient until the intermediary tubing has passed through the nasopharynx;

disconnecting the introducer from a first end of the intermediary tubing;

connecting the first end of the intermediary tubing to an inlet end of the airway ventilation device; and connecting a second end of the intermediary tubing to a gas supply to deliver gas from the supply to the outlet end of the airway ventilation device located in the airway of a patient.

The method may further comprise the step of connecting the inlet end of the airway ventilation device to the gas supply prior to passing the introducer through the nasopharynx. There may be a first intermediary tubing and a second intermediary tubing. The inlet end of the airway ventilation device may have a removable fitting configured to connect to a gas supply. The step of connecting the inlet end of the airway ventilation device to the gas supply may comprise connecting the removable fitting connected to the airway ventilation device to the gas supply or connecting the first intermediary tubing between the inlet end of the airway ventilation device and the gas supply. The intermediary tubing connected to the introducer may be the second intermediary tubing. In the case of a the removable fitting, it should be appreciated that the intermediary tubing connected to the introducer may be the only intermediary tubing.

The method may then also comprise disconnecting the inlet end of the airway ventilation device from the gas supply prior to connecting the first end of the intermediary tubing to the inlet end of the airway ventilation device.

The step of passing an introducer through the nasopharynx of a patient may include passing the blunt tip of the introducer through the nasopharynx first. The method may further comprise lubricating the introducer. The method may further comprise lubricating the intermediary tubing. The method may further comprise lubricating nostrils of the patient. The step of pulling the introducer through the mouth of the patient may comprise grasping the blunt end of the introducer with forceps, preferably Magill's forceps.

The method may further comprise the step of connecting the introducer to the intermediary tubing. The step of connecting the introducer to the intermediary tubing may comprise inserting a shaft of the introducer into an end of the intermediary tubing. The step of connecting the introducer to the intermediary tubing may comprise receiving the first end of the intermediary tubing within a socket of the introducer. The step of connecting the introducer to the intermediary tubing may comprise locating a protrusion of the shaft into an opening of the intermediary tubing.

According to another form there is provided a method of converting an orally intubated airway ventilation device to nasal intubation, the method including the steps of:

passing an introducer having a first end connected to intermediary tubing and a second end having a blunt tip through the nasopharynx of a patient;

pulling the introducer through the mouth of the patient until the intermediary tubing has passed through the nasopharynx;

disconnecting the introducer from a first end of the intermediary tubing;

disconnecting an inlet end of an orally intubated airway ventilation device from a gas supply;

connecting the first end of the intermediary tubing to the inlet end of the airway ventilation device; and connecting a second end of the intermediary tubing to the gas supply.

According to another form there is provided an intubation apparatus including:

an airway ventilation device having tubing located between an inlet end and an outlet end, the outlet end being configured to be locatable in the airway of a patient;

intermediary tubing, which may be solid, having a first end releasably connectable to the inlet end of the airway ventilation device;

an introducer having a first end releasably connectable to the first end of the intermediary tubing and a second end having a blunt tip; wherein:

the inlet end of the airway ventilation device has a removable fitting for interchangeable connection between a gas supply and the first end of the intermediary tubing;

the intermediary tubing is configured to be inserted into the nasopharynx of a patient by the introducer and then, once disconnected from the introducer and connected to the inlet end of the airway ventilation device, to pull the inlet end of the airway ventilation device through the nasopharynx of a patient for retrograde nasal intubation of the airway ventilation device.

According to another form there is provided a method of retrograde nasal intubation comprising:

inserting an outlet end of an airway ventilation device in the airway of a patient;

passing an introducer having a first end connected to intermediary tubing and a second end having a blunt tip through the nasopharynx of a patient;

pulling the introducer through the mouth of the patient until the intermediary tubing has passed through the nasopharynx;

disconnecting the introducer from a first end of the intermediary tubing;

connecting the first end of the intermediary tubing to an inlet end of the airway ventilation device; and pulling the intermediary tubing back through the nasopharynx of the patient until the inlet end of the airway ventilation device is external of the patient;

disconnecting the intermediary tubing from the inlet end of the now nasally intubated airway ventilation device; and connecting the inlet end of the nasally intubated airway ventilation device to a gas supply to deliver gas from the supply to the patient via the airway ventilation device.

According to another form there is provided a method of intubating a patient with an endotracheal tube comprising:

disconnecting a laryngeal mask located in the patient from a gas supply;

inserting an outlet end of an airway ventilation device comprising an endotracheal tube and intermediary tubing through the laryngeal mask;

deflating the laryngeal mask and removing it from the patient over the endotracheal tube to the intermediary tubing;

disconnecting the intermediary tubing from the endotracheal tube; and connecting the endotracheal tube to the gas supply to supply gas to deliver gas from the supply to the patient via the endotracheal tube.

Further features and advantages of the present invention will become apparent from the following detailed description.

BRIEF DESCRIPTION OF THE DRAWINGS

By way of example only, preferred embodiments of the invention will be described more fully hereinafter with reference to the accompanying figures, wherein.

DETAILED DESCRIPTION OF THE DRAWINGS

Figure 1:
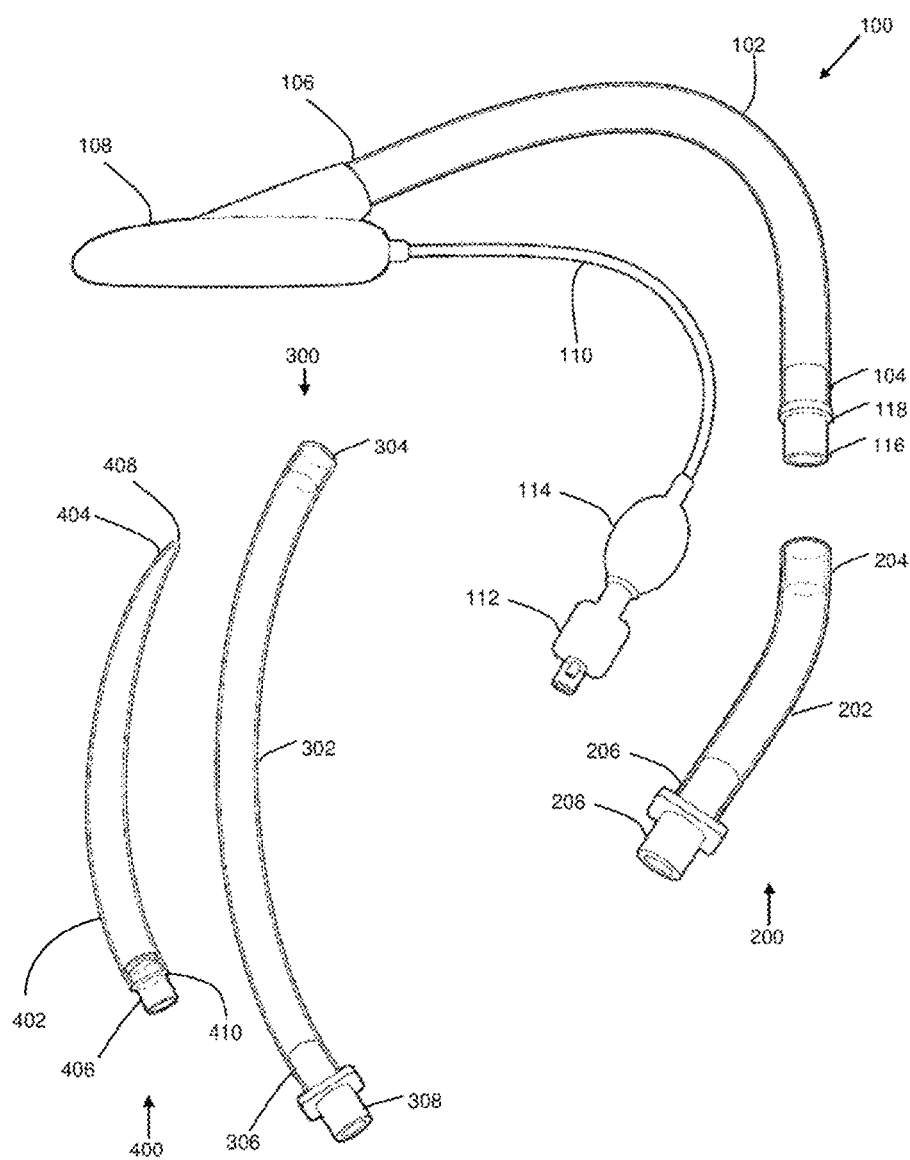
FIG. 1 illustrates components of an intubation apparatus.

FIG. 1 illustrates components of an intubation apparatus including an airway ventilation device in the form of a laryngeal mask 100 having ventilation tubing 102 having an inlet end 104 and an outlet end 106. The outlet end 106 has an inflatable cuff 108 configured to seal the glottis of a patient with the ventilation tubing 102 allowing passage of gas therethrough. The inflatable cuff 108 has an inflation chamber fluidly connected to an inflation line 110 which includes a valve 112 and a pilot balloon 114 at its opposite end.

The inlet end 104 of the laryngeal mask 100 has a connector 116. The connector 116 may be removable or include a removable component. In an alternative form the connector 116 may include, or be in the form of, a removable standard airway connector (see, for example, 208). In the illustrated embodiment the connector 116 has an outer diameter that is smaller than the outer diameter of the ventilation tubing 102. Whilst other connector forms are envisaged, including one in which the connector 116 has the same outer diameter as the ventilation tubing 102, it is preferable that the outer diameter of the connector 116 does not exceed the outer diameter of the ventilation tubing 102. The connector 116 is hollow, having a bore extending therethrough, that allows passage of gas. The outer diameter of the connector 116 is preferably sized to provide an interference fit with tubing of the size of the ventilation tubing 102.

It should be appreciated that the cuff 108 of the laryngeal mask 100 may include other designs to that illustrated to fit the laryngeal space isolating the supraglottic area of a patient. It may be inflatable, as illustrated, or soft and solid not requiring inflation. The size may vary to fit patients of different ages and weights. It may have a port for a nasogastric tube that feeds through the cuff 108 into the oesophageal aperture of a patient with the nasogastric tube being inserted through a contralateral nostril and inserted into a port in the oropharynx. The inflation line 110 may also be separated from the ventilation tubing 102, as illustrated, or may be included in the wall of the airway tubing. The balloon 114 and valve 112 may be able to be disconnected from the inflation line 110 to allow retrograde passage through the nasopharynx such that the balloon 114 and valve 112 may be located outside of, and connected to the cuff 108 via, the nostrils of the patient.

A first intermediary tubing 200 and a second intermediary tubing 300 are provided. The first intermediary tubing 200 being shorter than the second intermediary tubing 300. In general, the shorter intermediary tubing is more well suited to oral intubation and the longer intermediary tubing is more suited to nasal intubation. Apart from length the first intermediary tubing 200 and second intermediary tubing 300 are the same and will hereinafter be described concurrently.

The intermediary tubing 200, 300 includes ventilation tubing 202, 302 extending between a first end 204, 304 and a second end 206, 306. The first end 204, 304 is sized and shaped to be releasably connectable to the connector 116 of the inlet end 114 of the laryngeal mask 100. In the illustrated embodiment the interference connection is an interference fit with a portion of the connector 116 being inserted into the first end 204, 304.

It should be appreciated, however, that the arrangement may be reversed, with the connector 116 being located on the intermediary tubing and being inserted into the inlet end 104 of the laryngeal mask 100. It should also be appreciated that the connector 116 may be integral with one or more of the laryngeal mask 100 and the intermediary tubing 200, 300 or, alternatively, the connector 116 may be a separate component altogether to which the laryngeal mask 100 and the intermediary tubing 200, 300 both connect.

The connector 116 includes a hollow member in the form of a hollow body with a flange 118 having an annular hollow protrusion extending therefrom. The flange 118 has substantially the same shape and outer diameter as an outer diameter of the ventilation tubing 102 to provide a substantially continuous transition surface. The outer diameter of the hollow protrusion extending from the flange 118 is sized to create a removable interference fit with the first end 204, 304 of the intermediary tubing 200, 300. In an alternative form, the connector 116 may be integral with the inlet end 104 with or without such a flange 118.

At the second end 206, 306 of the intermediary tubing 200, 300 is a fitting in the form of a 15 mm airway connector 208, 308 for connection to a standard gas supply. Other suitable airway connectors could also be utilised.

Only one intermediary tubing 200, 300 is required for nasal or oral intubation, but by having two it is possible to intubate orally in the normal manner with the first intermediary tubing 200 connected to the laryngeal mask 100 and then convert to nasal intubation by disconnecting the orally intubated first intermediary tubing 200 and connecting the second intermediary tubing 300, once intubated nasally, with minimal disruption to airflow through the airway ventilation device.

It should be appreciated that the laryngeal mask 100 may have a standard gas source fitting, such as a 15 mm airway connector (cf. 208, 308), to which the first end 202, 302 of the intermediary tubing 200, 300 is correspondingly configured to connect. It should also be appreciated that the sizing, in particular the external diameter and internal diameter of the ventilation tubing 102, 202, 302 and connector 116, may be varied to according to the size of the cuff 108 of the laryngeal mask 100 to fit different patients according to weight, size, and age or to allow for atraumatic passage through the nasopharynx of a patient.

An introducer 400 is also provided. The introducer 400 is in the form of a tapered member having a first end 402 releasably connectable to the first end 302 of the intermediary tubing 300 and a second end 404 having a blunt tip 408. The introducer 400 is preferably curved and resiliently flexible. The first end 402 of the introducer 400 is releasably connectable to the first end 302 of the intermediary tubing 300 by having an introducer connector in the form of a shaft 406 insertable into the first end 302 of the intermediary tubing 300 and retainable therein by way of interference fit.

The shape of the shaft 406 of the introducer 400 is therefore preferably the same as, or at least substantially the same as, the shape of the connector 116 of the laryngeal mask 100 which preferably connects to the same end of the intermediary tubing in the same, or at least substantially the same, manner once the introducer has been disconnected therefrom. In an alternative form the first end 302 of the intermediary tubing 300 may be received by a socket of the introducer 400. In such a form the first end 302 of the intermediary tubing 300 is preferably the same, or at least substantially the same, as the inlet end 104 of the laryngeal mask 100.

A boss 410 is located adjacent the shaft 406 and first end 402 of the introducer. The boss 410 is preferably sized and shaped to correspond to the size and shape of the flange 118 of the laryngeal mask 100. The boss is preferably formed by an inward step from the body of the introducer 400 to the shaft 406. The boss is therefore preferably in the form of a radial ledge or shoulder around the shaft 406. In an alternative form (not illustrated) the introducer may have a socket configured to receive the first end 304 of the intermediary tubing 300.

The curve of the introducer 400 allows the device to be directed along the floor of the nasopharynx through the safer inferior passage beneath the inferior turbinate and negotiate the right angle at the junction of the nasal and oropharynx of a patient. The introducer 400 illustrated in FIGS. 1 and 3 is tapered substantially continually such that the introducer has a constantly increasing diameter from the blunt tip 408 (at the second end 404) to the boss 410 (adjacent the shaft 406 and first end 402).

Figure 2:
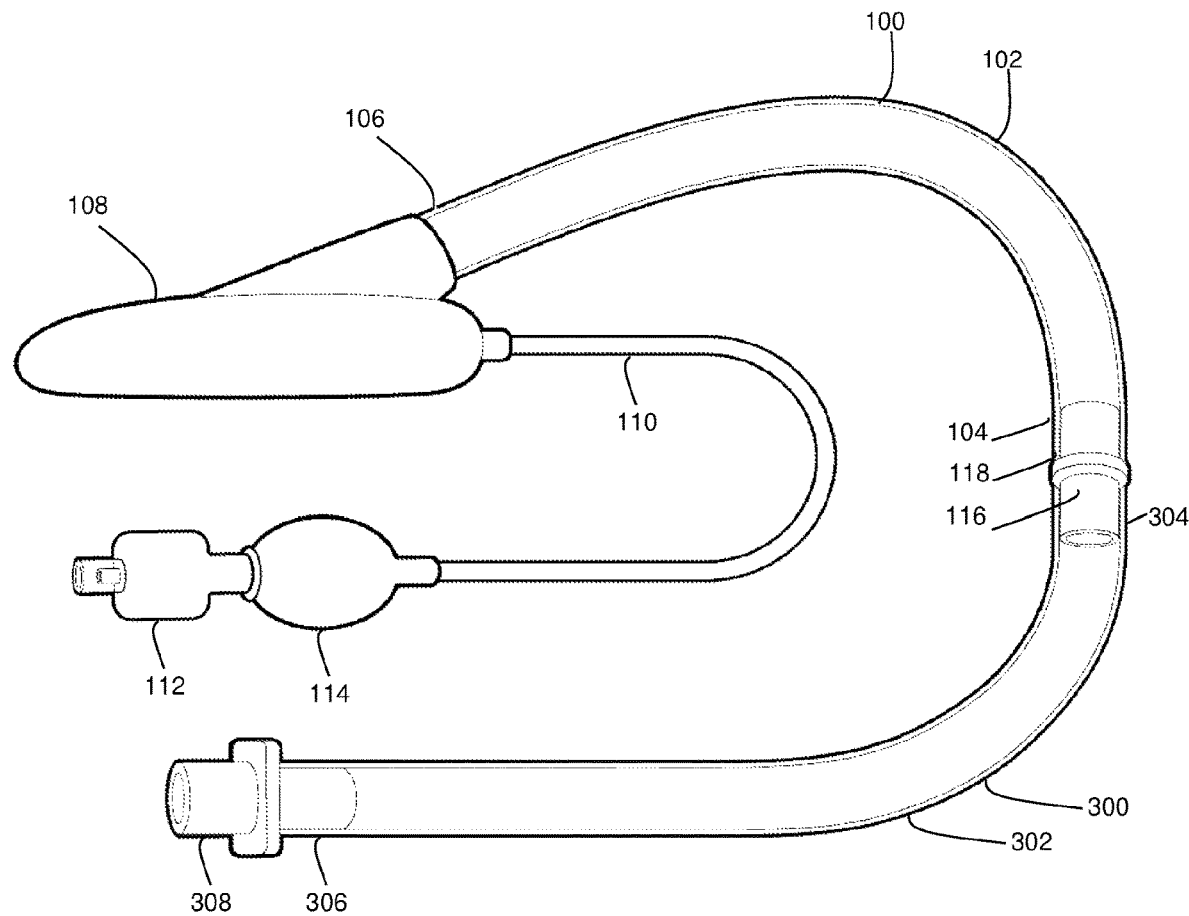
FIG. 2 illustrates components of the intubation apparatus of FIG. 1 when connected to intermediary tubing.

FIG. 2 illustrates the laryngeal mask 100 connected to the first end 304 of intermediary tubing 300. Notably the connection between the laryngeal mask 100 and intermediary tubing 300, via connector 116, is substantially seamless. The outer surface of the inlet end 104 of the laryngeal mask 100 extends substantially continuously to the first end 304 of the intermediary tubing 302. Although the longer intermediary tubing 300 is shown connected to the laryngeal mask 100, it should be appreciated that the shorter intermediary tubing 200 would connect in exactly the same manner. In an alternative form (not illustrated) the laryngeal mask 100 may have connector 116 that includes or consists of a removable fitting, such as a standard airway connector (see, for example, fitting 208 of intermediary tubing 200), that allows connection to a gas supply when the removable fitting is attached or connection to the first end of intermediary tubing 300 when the removable fitting is removed.

Figure 3:
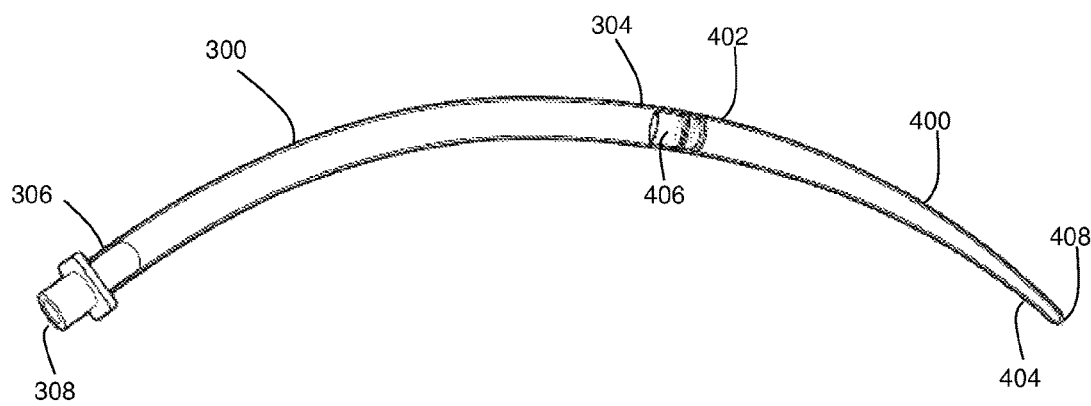
FIG. 3 illustrates an introducer component of FIG. 1 when connected to intermediary tubing.

FIG. 3 illustrates the introducer 400 connected to intermediary tubing 300 with the shaft 406 of the introducer 400 being received within the first end 304 of the intermediary tubing 300. The first end 304 of the intermediary tubing 300 abuts the boss 410 to provide a substantially seamless and continuous outer surface between the second end 406 of the introducer and the first end 304 of the intermediary tubing 300. In an alternative form (not illustrated) the first end 304 of the intermediary tubing 300 may be inserted into a socket of the introducer 400. In such a form it is preferred that the first end 304 of the intermediary tubing has a smaller outer diameter than its ventilation tubing portion 302 such that once the first end 304 is received within the socket of the introducer 400 the same substantially seamless and continuous outer surface between the second end 406 of the introducer and the first end 304 of the intermediary tubing 300 is provided.

Figure 4:
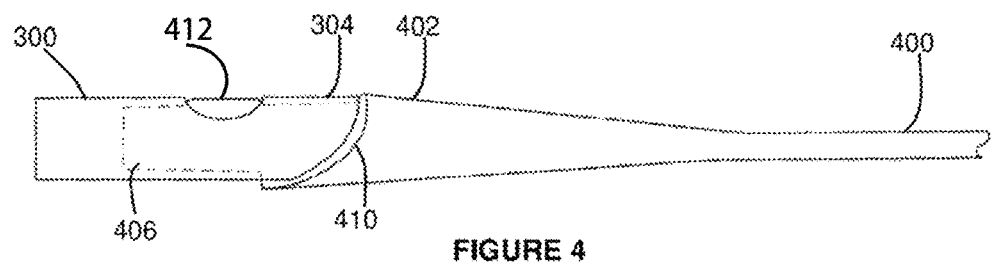
FIG. 4 illustrates a close up view of a connection region of an alternative introducer component when connected to intermediary tubing.

FIG. 4 illustrates a close up view of a connection region of an introducer 400 when connected to intermediary tubing 300. The introducer 400 illustrated in FIG. 4 has a projection 412 on the shaft 406. The projection 412 corresponds to a recess, in the form of an aperture, of the first end 304 of the intermediary tubing 300. The recess and projection 412 may be any suitable shape but they are preferably correspondingly circular or oval in shape.

The boss 410 of the introducer of FIG. 4 also shows an example curved shape that corresponds to a curved first end 304 of the intermediary tubing 300. It should be appreciated that different shaped intermediary tubing 300 first ends 304 could be used such as, for example, straight, bevelled, curved, Murphy, or Magill tip shaped and preferably the boss 410 of the introducer is shaped correspondingly to the first end 304 of the intermediary tubing 300.

Figure 5:
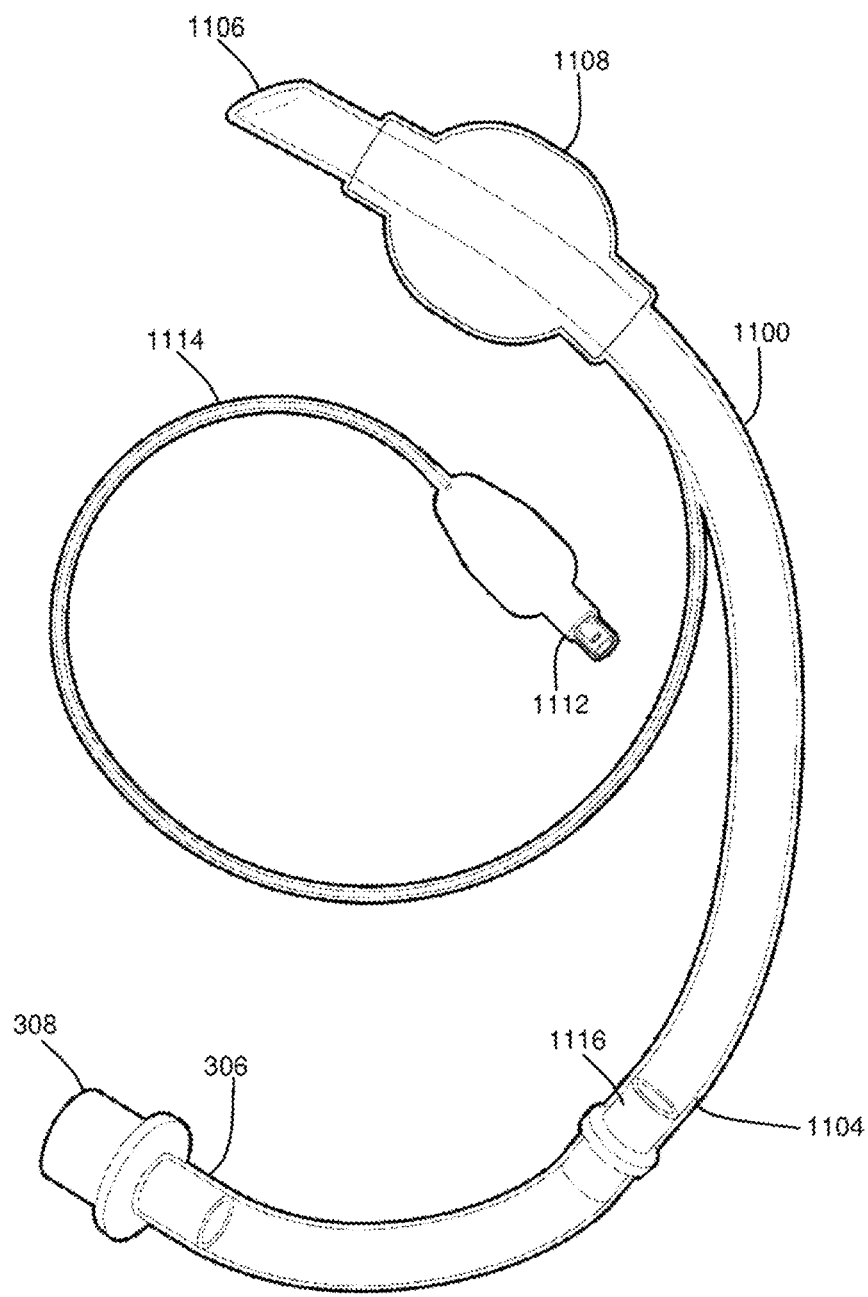
FIG. 5 illustrates components of an endotracheal tube intubation apparatus when connected to intermediary tubing.

FIG. 5 illustrates an airway ventilation device in the form of an endotracheal tube intubation apparatus 1100 rather than a laryngeal mask 100. The endotracheal tube 1100 of FIG. 5 is connected to intermediary tubing 200 similarly to how the laryngeal mask is configured in FIG. 2. The endotracheal tube 1100 is an alternative airway ventilation device that may be used instead of a laryngeal mask, and vice versa, depending on the situation.

The endotracheal tube 1100 has a ventilation tubing 1102 extending between an inlet end 1104 and an outlet end 1106. The endotracheal tube 1100 also has an optional inflatable cuff 1108 which is coaxially located with respect to the outlet end 1106 and a connector 1116 which is the same as connector 116 of FIGS. 1 and 2. The cuff 1108 has an inflation line 1114 with a valve and pilot balloon 1112 at a distal (relative to the cuff 1108) end thereof. As illustrated, the endotracheal tube 1100 is connected to intermediary tubing 200. As with the laryngeal mask 100 the ventilation tubing 1102 may be disconnectable and nasally intubated such that the inflation line is connected to the valve and pilot balloon 1112 via the nose of the patient.

In use, a laryngeal mask 100 or endotracheal tube 1100, preferably with a removable connector or connected to a first intermediary tubing 200 which effectively provides a detachable end, is placed into the larynx of a patient in the usual manner after induction of anaesthesia. The airway connector 208 of the intermediary tubing 200 is connected to a gas supply, preferably in the form of an anaesthetic machine, to continue ventilation and/or maintenance of anaesthesia.

After selecting the most appropriate nostril to intubate, a second intermediary tubing 300 is connected to the introducer 400. The nostril and tube are preferably both lubricated, and the device is passed through the nasopharynx of the patient with the blunt end 408 leading until the distal portion sits in the oropharynx with the laryngeal mask airway tubing 102. It should be appreciated that in certain circumstances this step may precede the insertion of the laryngeal mask 100 or endotracheal tube 1100 into the patient.

Using a laryngoscope under direct vision, the distal blunt end 408 of the introducer 400 is then grasped and delivered through the mouth of the patient with Magill's forceps or the like.

The introducer 400 is then disconnected from the second intermediary tubing 300 that has been passed through the nasopharynx. The first intermediary tubing 200 is also disconnected from the laryngeal mask 100 or endotracheal tube 1100 and may be removed. The second intermediary tubing 300, which is now nasally intubated, is then connected to the inlet end 100 of the laryngeal mask 100 or endotracheal tube 1100. The airway connector 308 of the second intermediary tubing 300 is then connected to the ventilation machine allowing continued ventilation and/or maintenance of anaesthesia.

Any excess tubing sitting in the mouth of the patient may be reduced by gentle traction on the airway tube at the external nares of the patient while the first end 304 connected to connector 116 of the laryngeal mask 100 or endotracheal tube 1100 is stabilised until the oropharyngeal portion of the intermediary tubing 300 sits snugly along the posterior wall of the oropharynx of the patient. The intermediary tubing may then be located out of the nose of the patient with the airway tubing 1100 sitting snug on the post wall of the oropharynx of the patient. The inflation line 110, balloon 114, and valve 112 may be taped out of a surgical field at the mouth of the patient or, alternatively, be stored in the oropharynx of the patient.

At the end of the surgical procedure while the patient is still under anaesthesia the nasal intubation steps may be reversed allowing the laryngeal mask 100 or endotracheal tube 1100 to be fluidly connected to the anaesthetic machine orally via the shorter first intermediary tubing 200.

Figure 6:
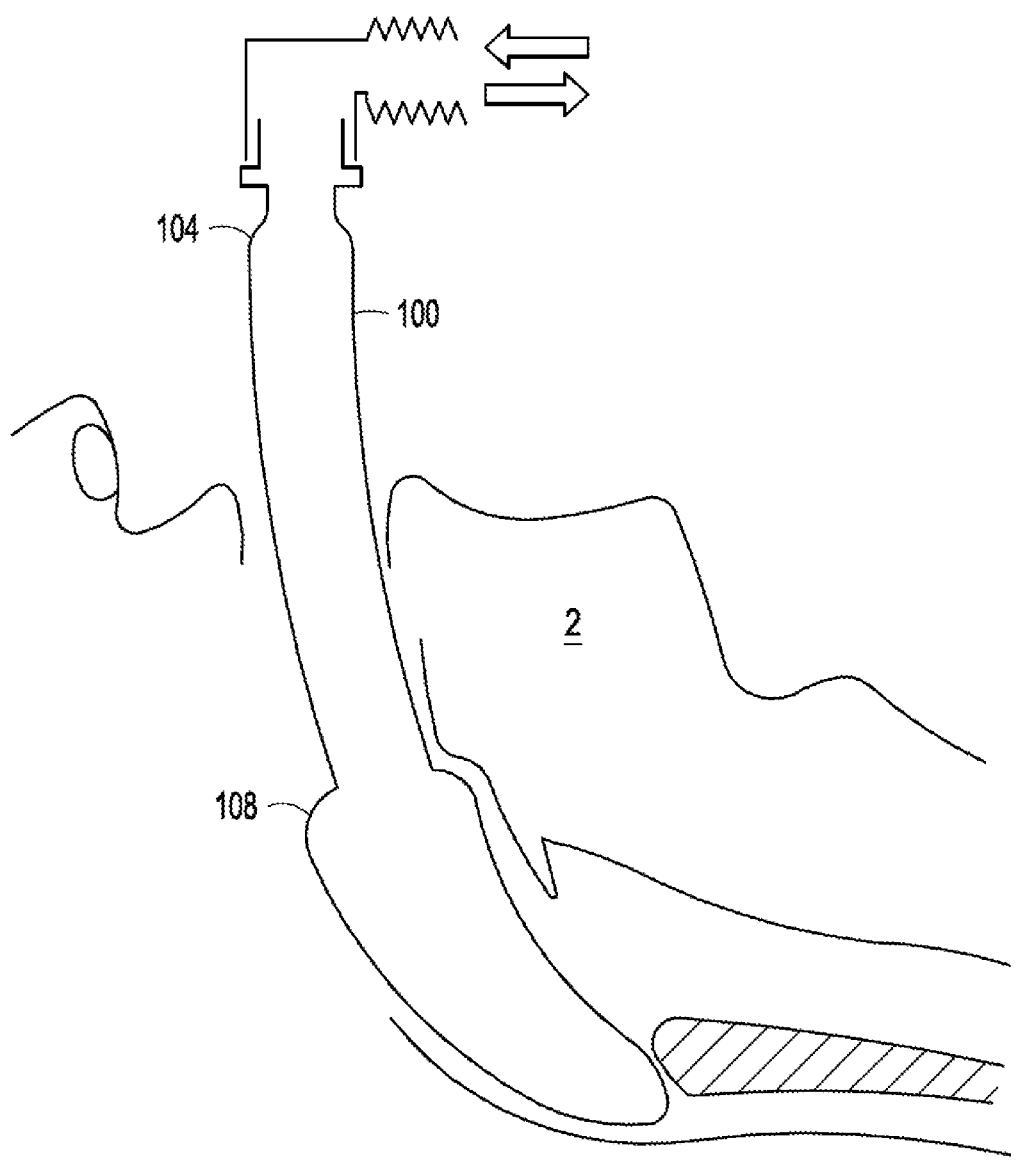
FIG. 6 illustrates a laryngeal mask located in the airway of a patient.
Figure 7:
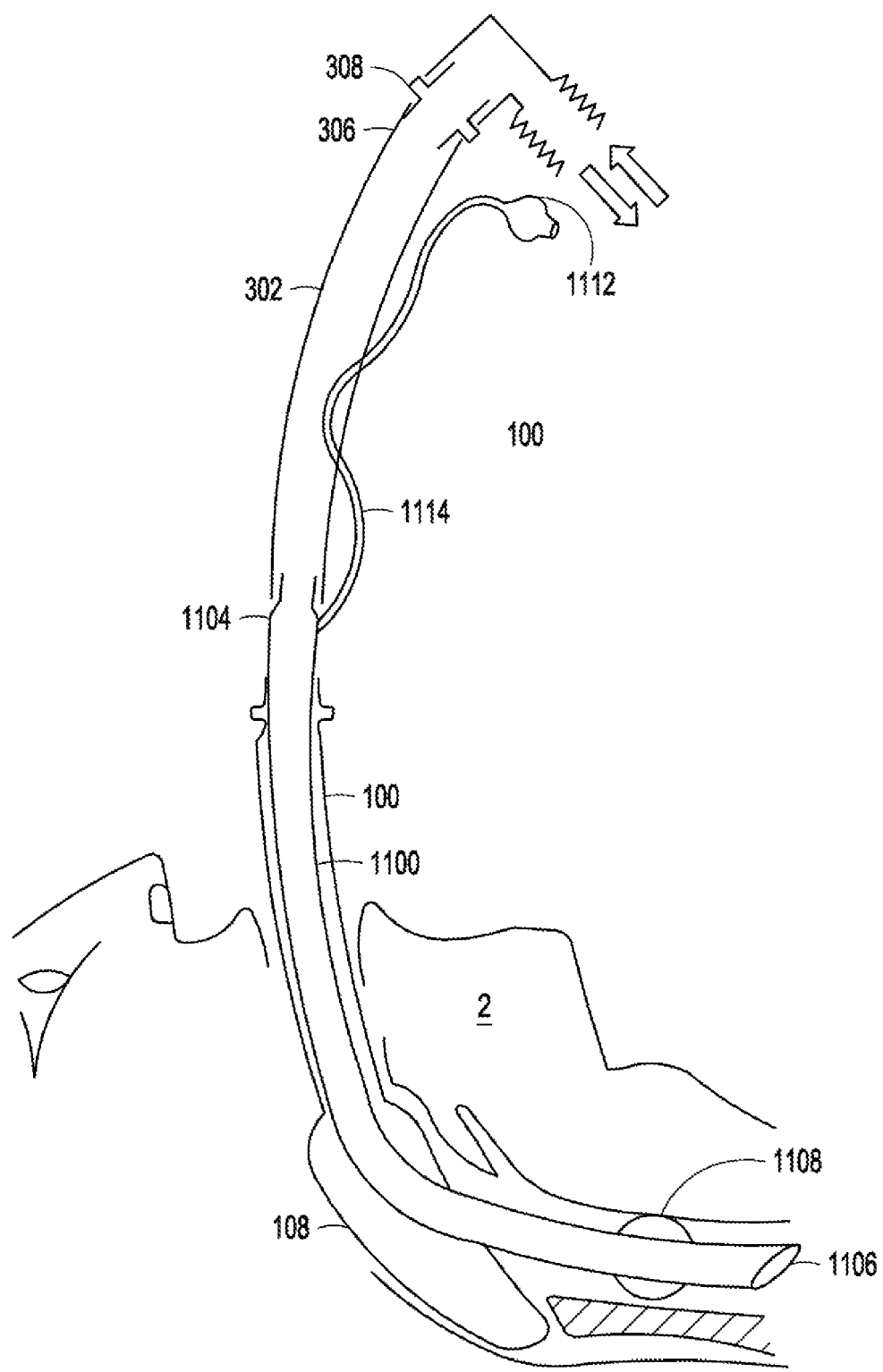
FIG. 7 illustrates an intubation apparatus inserted through the laryngeal mask of FIG. 6.

FIGS. 6 to 10 illustrate intubation of a endotracheal tube 1100 into a patient 2 though a laryngeal mask 100. FIG. 6 illustrates the laryngeal mask 100 located orally in an airway of the patient 2. FIG. 7 then shows the laryngeal mask 100 disconnected from the gas supply with the endotracheal tube 1100 inserted therethrough. The endotracheal tube 1100 is connected to the gas supply, via airway connector 308, to provide gas from the gas supply to the patient 2.

There are two main methods for inserting the endotracheal tube 1100 through the laryngeal mask 100, namely: blind insertion and over a fibreoptic bronchoscope. For the first, blind insertion, the endotracheal tube 1100 is passed through the laryngeal mask 100 and once it is at a sufficient length to be below the vocal cords of the patient 2 the cuff 1108 of the endotracheal tube 1100 is inflated and the patient 2 is ventilated through the endotracheal tube 1100. For the second, over a fibreoptic bronchoscope, the endotracheal tube is connected to the airway tubing and loaded over a fibreoptic scope (not shown). The endotracheal tube 1100 is passed into the laryngeal mask 100 and the cuff 1108 of the endotracheal tube 1100 is inflated to allow ventilation through the endotracheal tube 1100 joined to the airway tubing. The fibreoptic scope is passed through the airway tubing and endotracheal tube 1100 through the laryngeal mask 100 tubing and through the vocal cords into the trachea of the patient 2. The endotracheal tube 1100 cuff 1108 is deflated and is advanced over the fibreoptic scope until it is positioned below the vocal cords after which the cuff 1108 of the endotracheal tube 1100 is reinflated. The fibreoptic scope can then be removed and ventilation continues through the endotracheal tube 1100.

Figure 8:
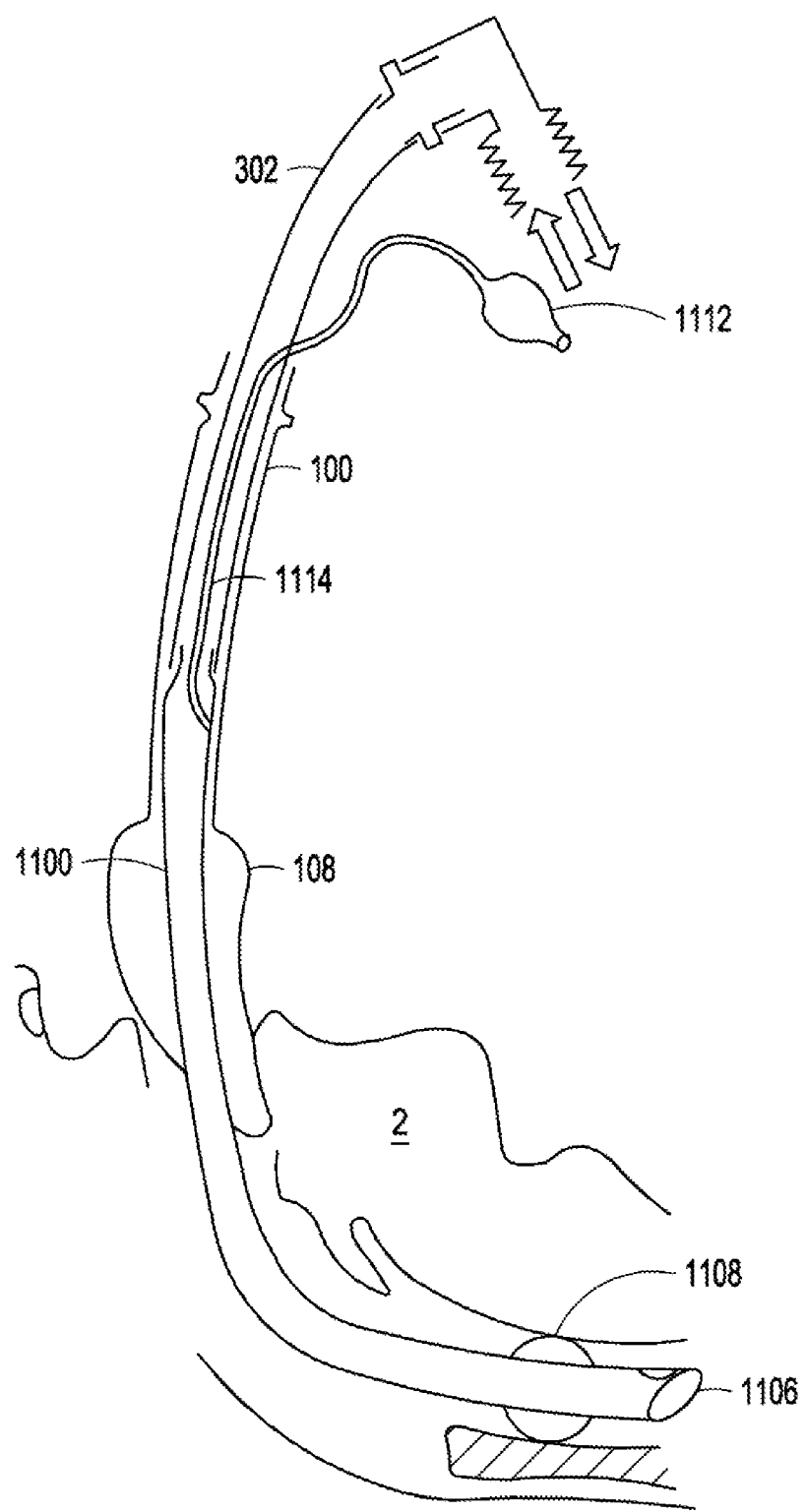
FIG. 8 illustrates partial removal of the laryngeal mask of FIG. 7.
Figure 9:
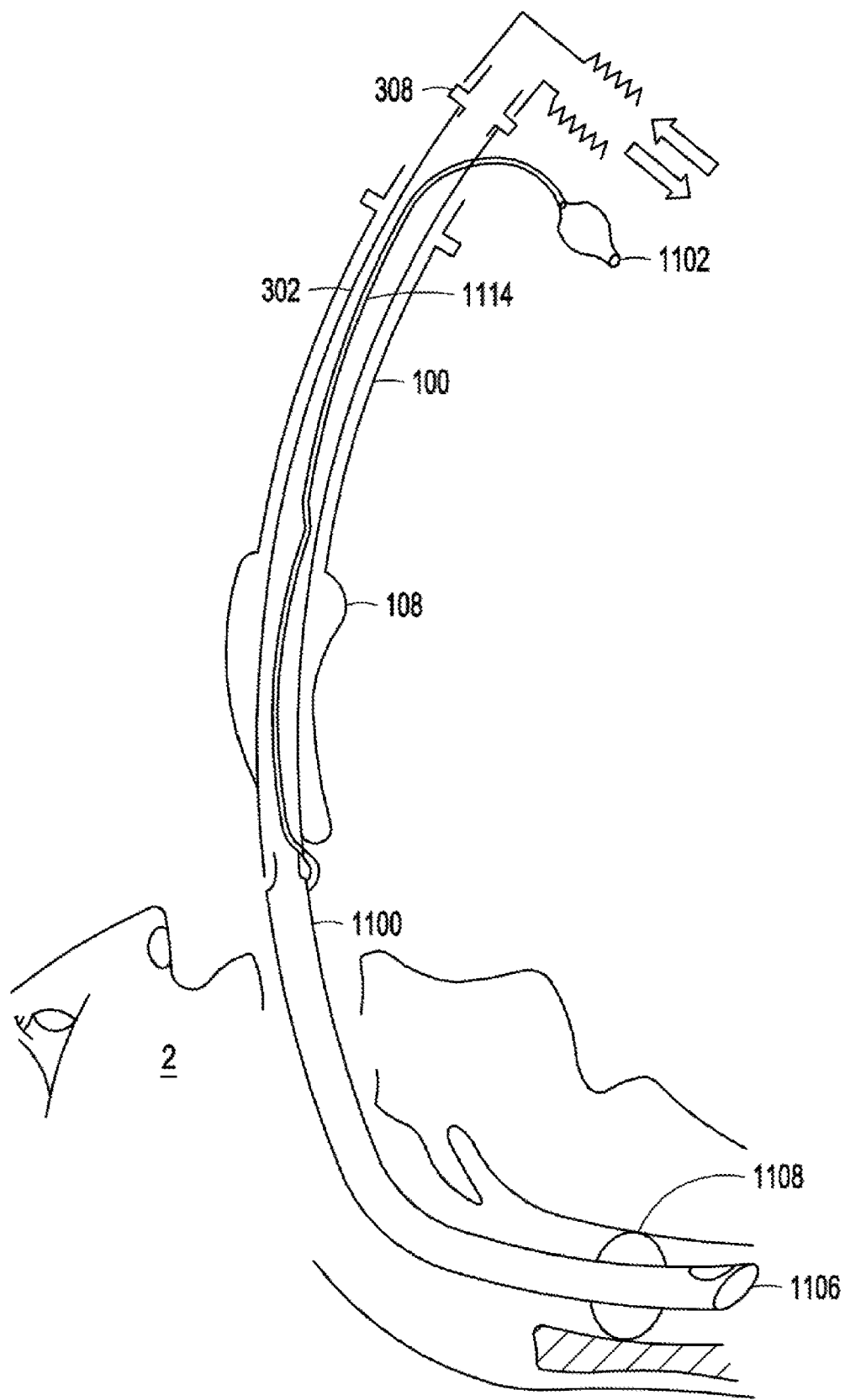
FIG. 9 illustrates further partial removal of the laryngeal mask of FIG. 8.
Figure 10:
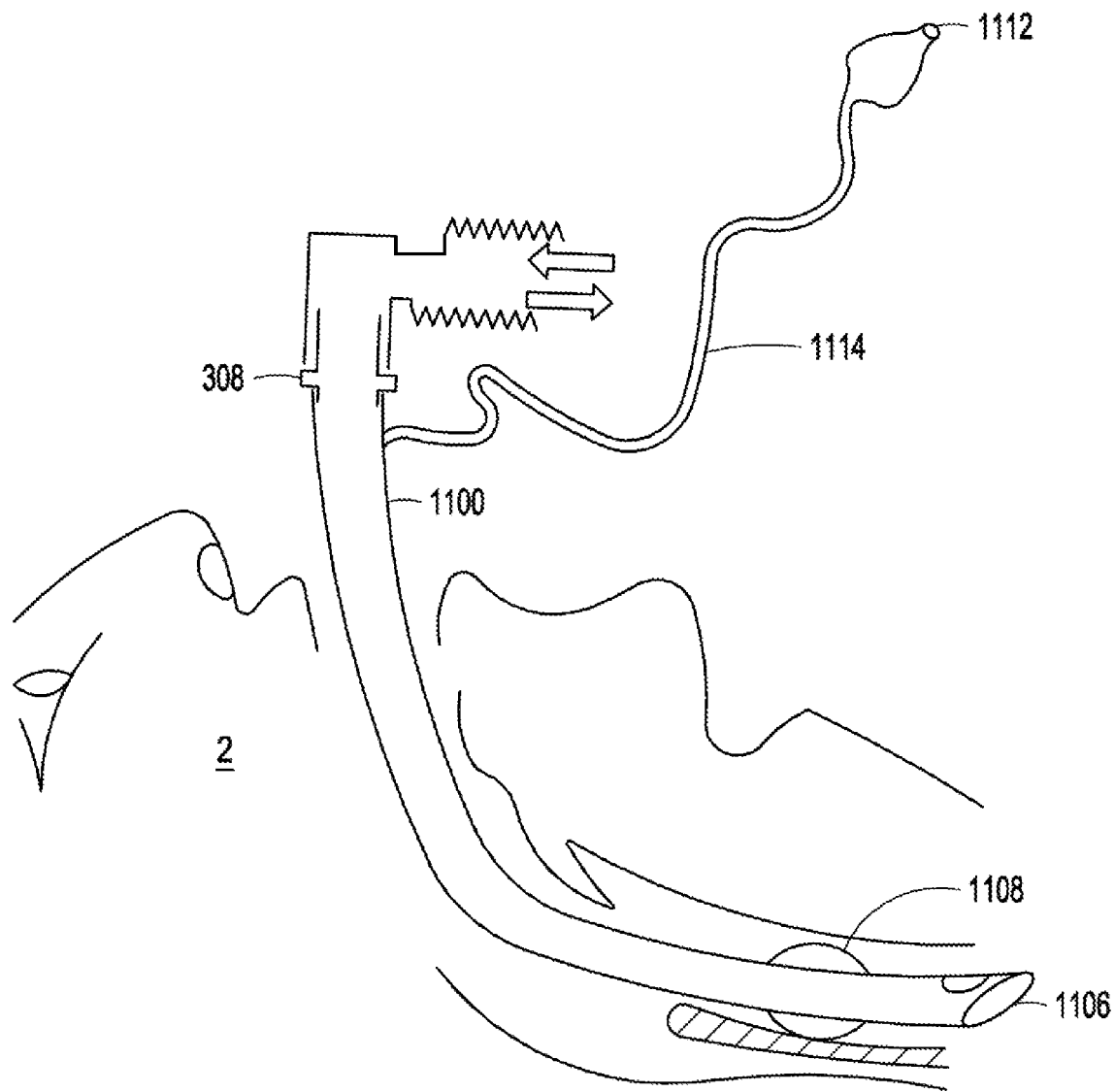
FIG. 10 illustrates the intubation apparatus of FIGS. 7 to 9 with lyrangeal mask removed.

As shown in FIGS. 8 and 9, the laryngeal mask 100 can then be removed from the patient 2. First the cuff 108 of the laryngeal mask 100 is deflated and the endotracheal tube 1100 stabilised. The laryngeal mask 100 is then pulled back through the oropharynx of the patient 2, over the endotracheal tube 1100 (as shown in FIG. 8) and onto ventilation tubing 302 (as shown in FIG. 9). The endotracheal tube 1100 is then disconnected from the ventilation tubing 302, the connector 308 is removed from the ventilation tubing 302 and connected to the endotracheal tube 1110, and the gas supply (not shown) is connected to the connector 308 in the endotracheal tube 1110 to supply gas to the patient 2. The disconnected ventilation tubing 302 may then be removed from the laryngeal mask 100, together with the inflation line 1114 (which remains connected to the endotracheal tube 1100). The patient 2 can then be supplied with gas via the endotracheal tube 1110 as illustrated in FIG. 10.

Advantageously, the intubation apparatus and method of use provide the ability to switch between oral and nasal intubation using the same airway ventilation device (e.g. laryngeal mask 100 or endotracheal tube 1100). Oral intubation can be converted to nasal intubation and vice versa. The gas supply to the patient is only disconnected briefly during conversion ensuring a substantially uninterrupted supply of gas.

The intubation apparatus is also relatively inexpensive and is intended to be disposable. The intubation apparatus ensures a patient can always be intubated by the optimal method including, for example, orally intubating the patient first to stabilise an airway and then, once ventilation has commenced, the patient can be nasally intubated to allow access to oral areas that may be obstructed by oral intubation.

Use of the introducer 400 provides relatively easy insertion through the nasopharynx whilst also preventing, or at least minimising, chances of inadvertently causing tissue damage or creating a haemorrhage. The introducer 400 also avoids the need to soften an endotracheal tube for insertion, which not only reduces the time needed to prepare for insertion, but also avoids associated problems from reduced integrity.

The introducer 400 initiates a pathway through the patient's orifice, with the taper providing a gentle and gradual expansion to the diameter of the first end 304 of the intermediary tube 300 allowing for gradual dilation of the nasopharynx to accommodate the diameter of the intermediary tube 300.

The abutment of the first end 304 of the intermediary tubing 300 with the boss 410 of the introducer 400 not only provides a substantially continuous surface between the intermediary tubing 300 and the introducer 400, but also provides a stable connection between the two. The boss 410 also prevents sliding of the introducer 400 further into the intermediary tubing 300 as it is pushed through an orifice. It further prevents any soiling of the first end 204 intermediary tubing 300.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step etc.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'includes', 'including', 'includes', 'including', or similar terms are intended to mean a non-exclusive inclusion, such that a method, system or apparatus that includes a list of elements does not include those elements solely, but may well include other elements not listed.

The invention claimed is:

1. A method of intubating a patient, the method including:
   inserting an outlet end of an airway ventilation device in an airway of the patient;
   passing an introducer having a first end connected to an intermediary tubing and a second end having a blunt tip through the nasopharynx of the patient;
   pulling the introducer through the mouth of the patient until the intermediary tubing has passed through the nasopharynx;
   disconnecting the introducer from a first end of the intermediary tubing;
   connecting the first end of the intermediary tubing to an inlet end of the airway ventilation device; and
   connecting a second end of the intermediary tubing to a gas supply to deliver gas from the supply to the outlet end of the airway ventilation device located in the airway of the patient.

2. The method of claim 1, further comprising the step of connecting the inlet end of the airway ventilation device to the gas supply prior to passing the introducer through the nasopharynx.

3. The method of claim 1, wherein the step of passing the introducer through the nasopharynx of the patient includes passing the blunt tip of the introducer through the nasopharynx first.

4. The method of claim 1, further comprising the step of connecting the introducer to the intermediary tubing.

5. A method of converting an orally intubated airway ventilation device to nasal intubation, the method including the steps of:
   passing an introducer having a first end connected to an intermediary tubing and a second end having a blunt tip through the nasopharynx of a patient;
   pulling the introducer through the mouth of the patient until the intermediary tubing has passed through the nasopharynx;

disconnecting the introducer from a first end of the intermediary tubing;
disconnecting an inlet end of an orally intubated airway ventilation device from a gas supply;
connecting the first end of the intermediary tubing to the inlet end of the airway ventilation device; and
connecting a second end of the intermediary tubing to the gas supply.

* * * * *